United States Patent
Rossi et al.

(10) Patent No.: US 6,247,485 B1
(45) Date of Patent: Jun. 19, 2001

(54) MINIATURE VALVE FOR FILLING THE RESERVOIR OF AN APPARATUS FOR THE TRANSDERMAL ADMINISTRATION OF MEDICINE

(75) Inventors: Carole Rossi, Ramonville; Philippe Millot, Orgeux; Daniel Esteve, Ramonville St Anne; Claude Mikler, Dijon; Eric Teillaud, Talant, all of (FR)

(73) Assignee: Laboratoires d'Hygiene et de Dietetique (L.H.D.), Paris (FR)

( * ) Notice: Subject to any disclaimer, the term of this patent is extended or adjusted under 35 U.S.C. 154(b) by 0 days.

(21) Appl. No.: 09/285,000
(22) PCT Filed: Nov. 20, 1997
(86) PCT No.: PCT/FR97/02101
    § 371 Date: Jul. 20, 1999
    § 102(e) Date: Jul. 20, 1999
(87) PCT Pub. No.: WO98/22719
    PCT Pub. Date: May 28, 1998

(30) Foreign Application Priority Data

Nov. 21, 1996 (FR) .................................................. 96 14230
May 29, 1997 (FR) .................................................. 97 06613

(51) Int. Cl.⁷ .............................. A61M 5/00; A61N 1/30
(52) U.S. Cl. .................... 137/68.13; 424/449; 604/20; 607/153
(58) Field of Search ............................... 137/68.11, 68.13; 424/449; 604/20; 607/153

(56) References Cited

U.S. PATENT DOCUMENTS

| 3,184,097 | | 5/1965 | Kilmer et al. ........................... 220/47 |
| 5,135,479 | * | 8/1992 | Sibalis et al. ........................... 604/20 |
| 5,186,001 | | 2/1993 | Muntz et al. ........................... 60/515 |
| 5,310,404 | * | 5/1994 | Gyory et al. ........................... 604/20 |

FOREIGN PATENT DOCUMENTS

| 0 513 879 | 11/1992 | (EP) . |
| WO94/21314 | 9/1994 | (WO) . |

\* cited by examiner

*Primary Examiner*—Michael Buiz
*Assistant Examiner*—Ramesh Krishnamurthy

(57) ABSTRACT

A miniature valve for filling the reservoir of an apparatus for the transdermal administration of a medicine including a) a substrate, b) a fuel charge arranged on the substrate opposite the passage to be opened through it, and c) an electric resistor placed in contact with the fuel charge so that the supply of this resistor with a predetermined electric energy ensures the combustion of the charge and the opening of the passage by local rupture of the substrate under the pressure of the fuel gases of the charge. The device is useful for filling a medicine reservoir for the transdermal administration medicine aided by inophoresis.

19 Claims, 3 Drawing Sheets

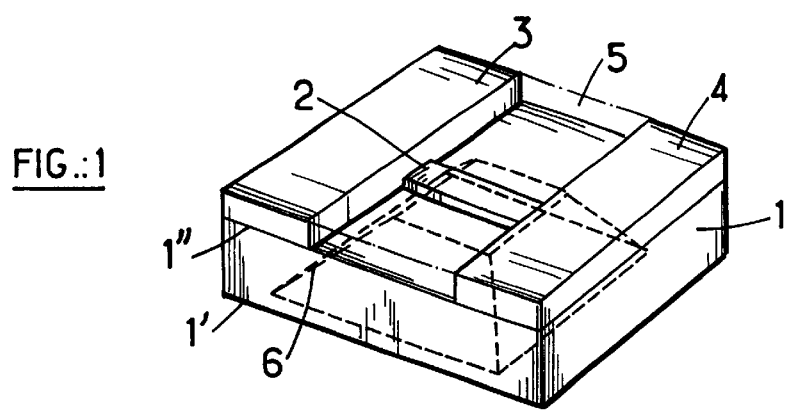
FIG.:1
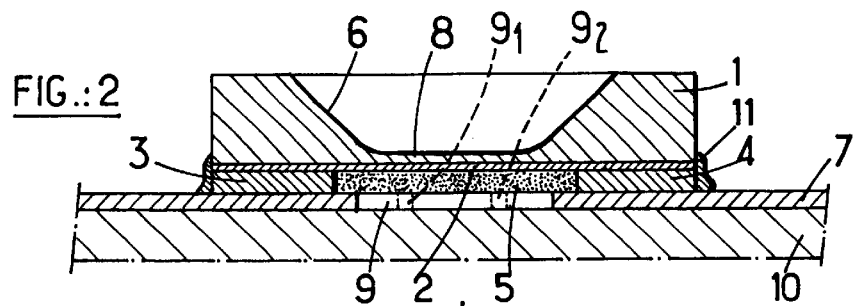
FIG.:2
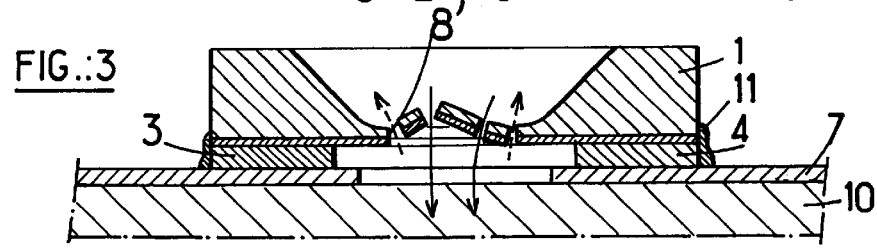
FIG.:3
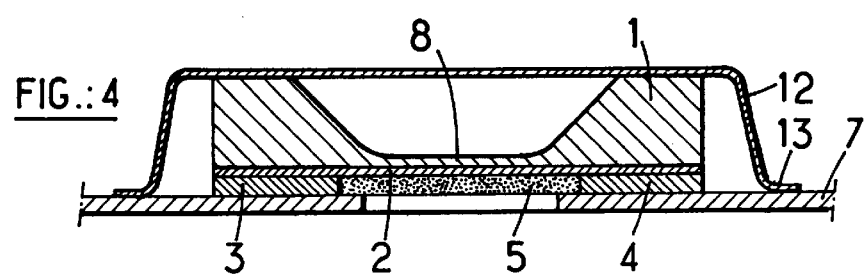
FIG.:4
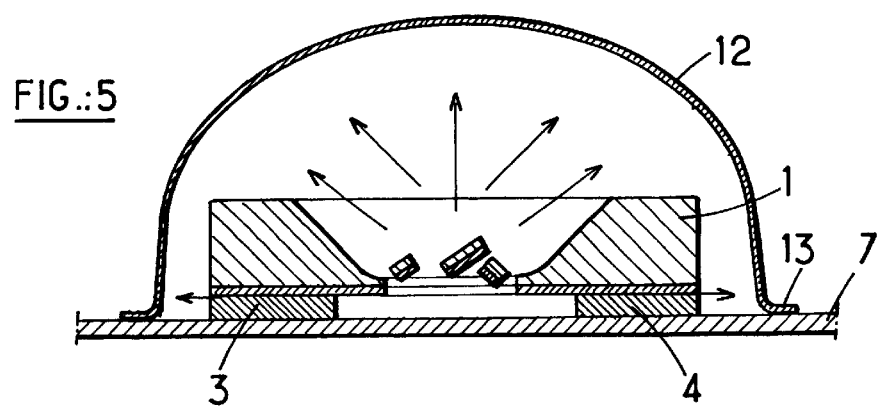
FIG.:5

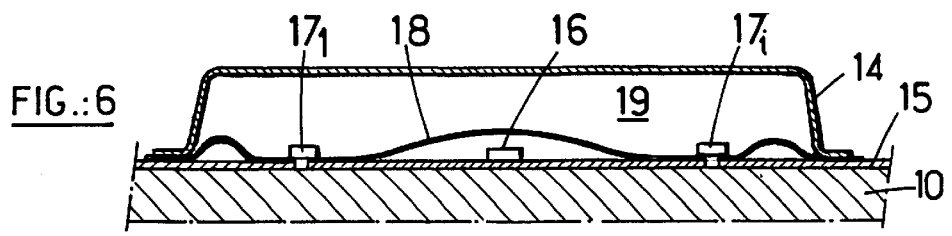
FIG.:6
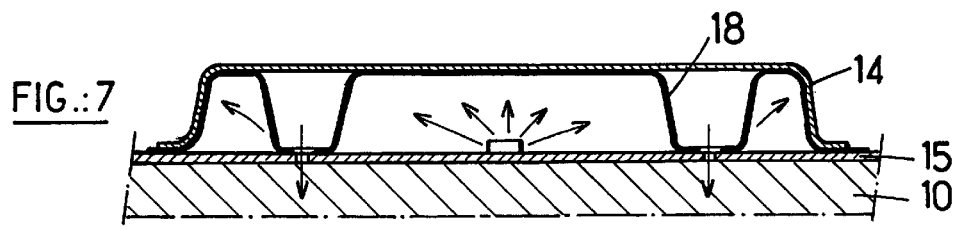
FIG.:7
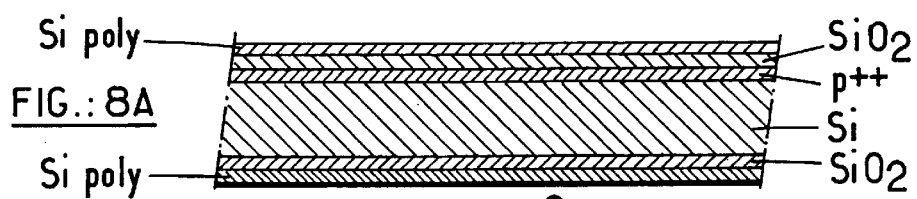
FIG.:8A
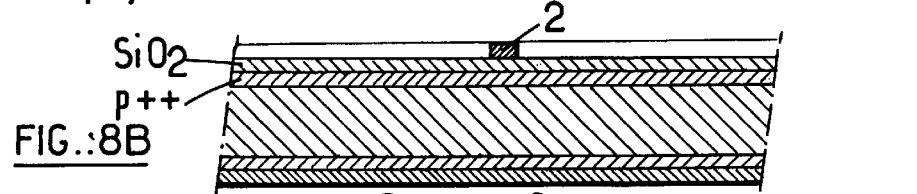
FIG.:8B
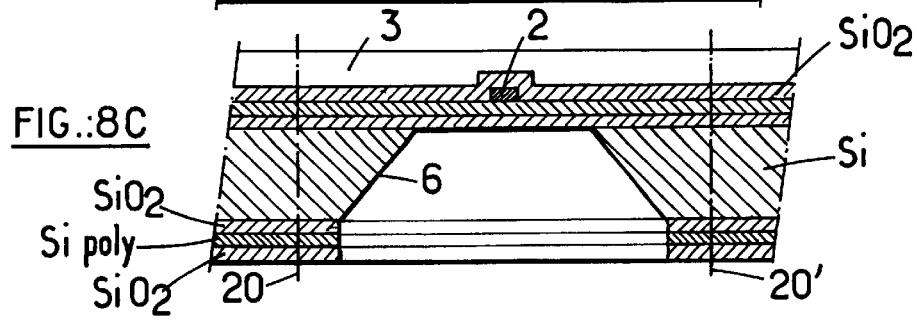
FIG.:8C
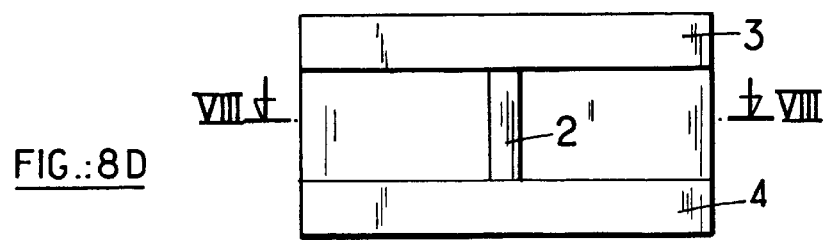
FIG.:8D
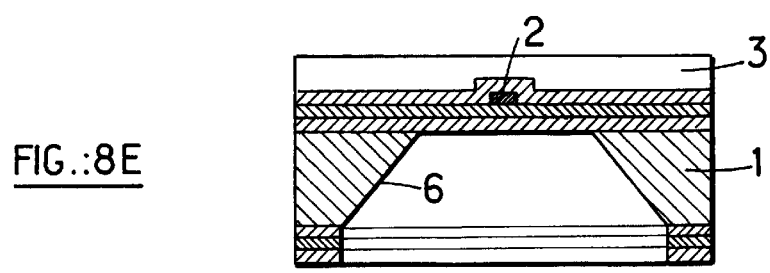
FIG.:8E

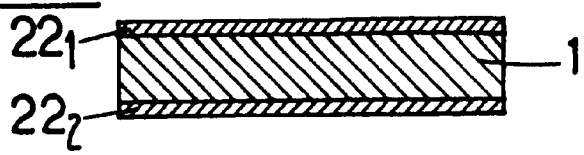
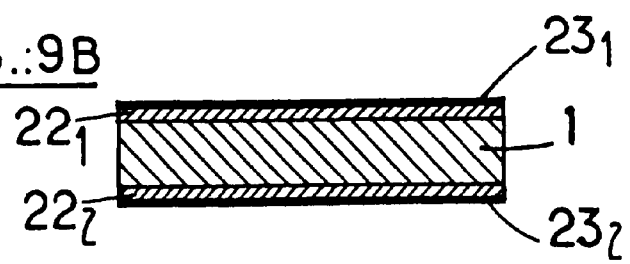
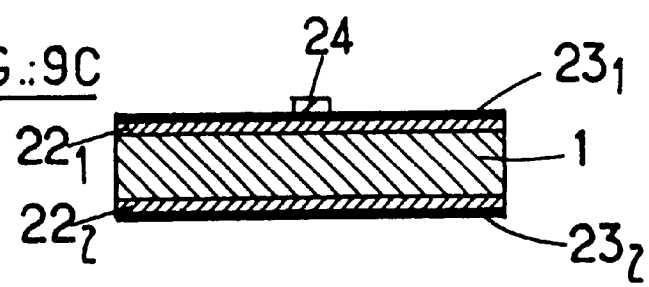
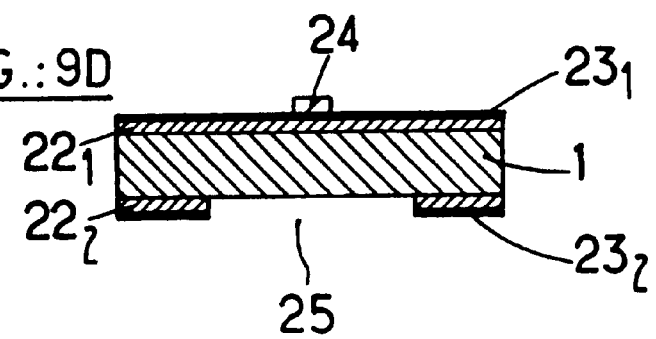
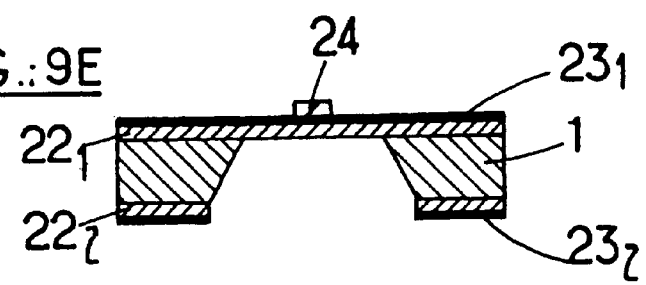

MINIATURE VALVE FOR FILLING THE RESERVOIR OF AN APPARATUS FOR THE TRANSDERMAL ADMINISTRATION OF MEDICINE

The present invention concerns a miniature valve, a device for filling a reservoir including a valve of this kind and a method of manufacturing said valve. The present invention also concerns apparatus for transdermal administration of medication including a device of this kind for filling a reservoir with a solution of an active principle to be administered.

For transdermal administration of a medication, a reservoir containing an active principle is generally applied to the skin of the patient, this reservoir routinely comprising a layer of a hydrophilic product such as a hydrogel carried by a suitable support. When administration of the medication is assisted by inophoresis, the active principle is in ionic solution. The ionic solution is stored in a sachet that is emptied into the reservoir immediately before administration. This procedure is necessary because the solution loses its stability in the hydrogel constituting the reservoir and therefore cannot be loaded into the latter ab initio.

The problem then arises of emptying the sachet of the active principle ionic solution into the reservoir. Various mechanical means have been designed for this, for example syringe type means in which actuation of a piston expels the ionic solution from the syringe to inject it into the reservoir. Flexible sachets have also been designed that are opened by puncturing or tearing them and emptied into the reservoir by applying pressure to the sachet.

It is therefore apparent that, whatever means are employed to empty the sachet of ionic solution into the reservoir, human intervention is required, which is impractical and does not lend itself to automatic initiation immediately prior to starting treatment. Moreover, the mechanical means referred to hereinabove are subject to deficiencies where sealing is concerned and do not always assure complete emptying of the sachet into the reservoir.

Transdermal administration of medication assisted by ionophoresis often employs equipment in the form of a bracelet worn by a patient, the bracelet carrying all of the units needed for this administration, so as to assure the autonomy of the patient. The bracelet therefore carries, in addition to the reservoir applied to the skin of the patient, electrodes, electronic control means for the electrodes and a battery electrical power supply for these means, which necessarily hold a limited quantity of electrical energy. It would be desirable for the emptying of the ionic solution into the reservoir mentioned above, also known as "hydrating" the reservoir, to be controlled by the electronic means incorporated into the bracelet so as to automate this emptying prior to a treatment, without this additional function of these means consuming more electrical energy than the battery can provide.

One aim of the present invention is to provide a miniature valve adapted to assure said "hydration" of the reservoir automatically, under the control of said electronic means, for a minimal expenditure of electrical energy that is not likely to compromise the operation of the portable equipment used for transdermal administration assisted by ionophoresis.

Another aim of the present invention is to provide a valve of this kind that eliminates the problems of sealing and of incomplete emptying of the sachet that sometimes affect the mechanical means for hydrating the reservoir used in the prior art.

Another aim of the present invention is to provide such a valve that can be manufactured industrially with a very low or event zero reject rate.

These aims of the invention, and others that will emerge from a reading of the following description, are achieved with a miniature valve comprising a) a substrate, b) a charge of a combustible material disposed on the substrate facing a passage to be opened through the latter, c) an electrical resistance in contact with the combustible charge so that supplying a predetermined electrical energy to this resistance assures the combustion of the charge and the opening of the passage by localised rupture of said substrate due to the pressure of the gases of combustion of the charge.

As will emerge below, placing a plurality of such valves between a sachet of an active principle solution and a reservoir to be charged with the solution provides means for automatic initiation of hydration of the reservoir immediately prior to a treatment without human intervention, simply by electronically commanding opening of these valves.

In accordance with other features of the present invention, the resistance is filamentary and the charge extends over and beyond the resistance, so that the heat generated by the resistance when supplied a predetermined quantity of electrical energy is initially concentrated in the portion of the charge that surrounds the resistance. Said predetermined electrical energy is less than 10 Joules. An expenditure of energy of this magnitude does not significantly drain the charge of the battery power supply of portable apparatus for transdermal application of medication assisted by ionophoresis and is therefore compatible with other demands for energy from the battery.

In accordance with another feature of the present invention, the charge and the resistance are disposed on the same side of a thinner area of the substrate, the thickness and the surface area of which are chosen so that the pressure of the gases due to the combustion of the charge fragments this area and opens it to the passage of said gases and possibly other fluids.

The invention therefore provides a device for filling a reservoir with a fluid contained in a sachet adjacent the reservoir, comprising at least one miniature valve in accordance with the invention disposed so as to block fluid communication between the sachet and the reservoir and means for selectively commanding energisation of the electrical resistance of the valve and thereby to cause the opening of said communication to the fluid contained in the sachet through the passage opened in the substrate of the valve by the combustion of the charge that it carries.

In accordance with another feature of this device, it further comprises at least one flexible envelope inside the sachet, this envelope containing a miniature valve in accordance with the present invention, the control means selectively initiating combustion of the charge carried by this valve so as to inflate the envelope with the combustion gas so as to assist the emptying of the sachet through the valve or valves disposed in fluid communications between said sachet and said reservoir.

The invention also provides a method of manufacturing the valve in accordance with the invention, wherein:
 a) a substantially plane face of a semiconductor material substrate is covered with an etch stop layer resistant to a solution for etching said material;
 b) said etch stop layer is covered with an electrically insulative layer if the etch stop layer is not electrically insulative;
 c) an electrical resistance is formed on said electrical insulation layer,
 d) the substrate is etched from the face of the substrate opposite that which carries said resistance as far as the etch stop layer, and e) a combustible charge is deposited on top of the electrical resistance.

Other features and advantages of the present invention will emerge from a reading of the following description and from an examination of the accompanying drawings, in which:

FIG. 1 is a schematic perspective view of a miniature valve in accordance with the present invention, FIGS. 2 and 3 are schematic sectional views of the valve from FIG. 1 used to explain how the latter works, FIGS. 4 and 5 show one particular embodiment of the miniature valve of the invention inside an inflatable envelope, FIGS. 6 and 7 are schematic illustrations of the structure and the operation of a device for filling a reservoir with a solution of active principle, with a view to transdermal application of this active principle, this device including miniature valves in accordance with the invention, and FIGS. 8A to 8E show the successive steps of a method of manufacturing the miniature valves of the invention.

FIGS. 9A to 9E show the successive steps of a variation of the method illustrated on FIGS. 8A to 8E.

FIG. 1 of the accompanying drawings shows a miniature valve in accordance with the invention that is parallelepiped shape in this non-limiting illustrative example. It comprises a substrate 1 carrying an electrical resistance 2 the ends of which are connected to metal contacts 3, 4, the resistance 2 being covered with a thin film of a charge 5 of a combustible material between the contacts 3, 4, shown as if it were transparent to clarify the figure.

When it burns, this material must form combustion gases necessary for the valve to operate, as explained below. In this non-limiting illustrative example only, a pyrotechnic material of the nitrocellulose or propergol type may be chosen for this purpose, for example. Successful results have been obtained with GB nitrocellulose, and in particular GBPA nitrocellulose as well as a propergol based on glycidyl polyazide sold by the French company Société Nationale des Poudres et Explosifs (S.N.P.E.). These nitrocelluloses and propergols can be ignited with minimum thermal energy, making them particularly appropriate for the present invention, as will emerge below.

The substrate 1 of the valve from FIG. 1 can be made from a single conductive material such as silicon, which is routinely used in the fabrication of integrated circuits. The valve in accordance with the invention can be fabricated by these techniques, as will be explained with reference to FIGS. 8A through 8E, so that it can be greatly miniaturised to the scale of an electronic "microchip", for example, enabling it to be integrated into compact equipment such as autonomous apparatus for transdermal administration of medication assisted by ionophoresis, described below with reference to FIGS. 6 and 7.

FIG. 1 also shows that the substrate 1 of the valve has a crater 6 in the shape of a truncated pyramid recessed into its face 1' which is parallel to and opposite that (1") which carries the resistance 2, the bottom of this crater consisting of a thinner area 8 of the substrate 1 adjoining the resistance. As will emerge below, the thickness of this thinner area 8 must be sufficiently small for this area to rupture due to the pressure of the gas generated by the combustion of the charge 5, initiated by heating by means of the resistance 2 on the same side of the thinner area as the charge 5.

FIGS. 2 and 3 show the valve or "chip" from FIG. 1 mounted on a printed circuit 7 adapted to pass an electrical current through the resistance 2, between the contact terminals 3 and 4 soldered to conductive tracks of this circuit, in a similar manner to that in which conventional electronic components are mounted on such circuits. At the location of the thinner area 8 of the substrate, there is a hole 9 through the circuit 7, this hole being closed off by a layer 10 of a product which, in the application to transdermal administration of medication envisaged above, can be a hydrogel to be charged with a solution of an active principle contained in a sachet communicating with the crater 6 of the substrate. Thus the charge 5 of combustible material is disposed between this layer 10 and the thinner area of the substrate. A seal 11 surrounds the substrate 1 to fix the substrate to the circuit 7 and to seal the space containing the charge 5.

It will be noted that the resistance 2 (FIG. 1) is elongate or filamentary and is therefore adjacent only a portion of the charge 5 that covers it.

By virtue of the printed circuit 7, the passage of an electrical current into the resistance 2 can be initiated automatically, under the control of a microprocessor, for example, also used conventionally to command the execution of a medication administration programme.

The current flowing through the resistance generates heat, by the so-called Joule effect, which, because of the low thermal conductivity of the nitrocellulose constituting the charge 5, remains concentrated in the charge around the resistance. This causes vigorous localised heating of the nitrocellulose, which ignites it. It will be noted therefore that igniting a portion of the nitrocellulose requires only a small quantity of electrical energy, which is advantageous when this energy is obtained from a battery supplying power to all of a portable apparatus for transdermal administration of medication assisted by ionophoresis. This greatly reduces the energy drain from the battery required to ignite the nitrocellulose, and this product is well suited to the intended application of the invention since it can be ignited locally at low temperatures with immediate propagation of combustion throughout the volume of the charge.

The quantity of nitrocellulose burned can be adjusted so that when the combustion of the nitrocellulose has generated a substantial quantity of gas within a small volume (that of the hole 9) the pressure in the hole reaches a value sufficient to rupture and dislocate the thinner area 8 of the substrate adjacent the hole 9 (see FIG. 3), this thinner area 8 being then replaced by a passage 8' allowing the gases formed to escape, as shown schematically by the dashed line arrow. It also allows a liquid in communication with the crater 6 to pass through the passage 8' and the hole 9 as shown by the solid line arrow, to impregnate the layer 10 of hydrogel constituting a transdermal medication administration apparatus reservoir, for example.

The large hole 9 pierced through circuit 7 can be replaced by a plurality of smaller off-centered holes $9_1, 9_2$, etc . . . , shown in dashed lines on FIG. 2, of cumulative area smaller than the one of hole 9. One can thus overcome the possible brittleness of layer 10, to enclose the gas originated from the combustion of charge 5.

A miniature valve in accordance with the invention has been made on a 3 mm×3 mm substrate carrying a charge of about $8.10^{-4}$ g of nitrocellulose forming on combustion 8 ml of gas at a pressure sufficient to destroy a thinner area 8 approximately 3 to 5 µm thick after passing 1 W of electrical power through the resistance for one second.

It is therefore apparent that the invention achieves the stated aims, namely providing a miniature valve, taking the form of an electronic chip, that can be triggered automatically by means of a low-power electrical signal, compatible with what is available from a battery power supply of a portable electronic apparatus, such as an apparatus for transdermal administration of medication assisted by ionophoresis.

FIGS. 4 and 5 show a particular arrangement of the valve in accordance with the invention, serving as a gas generator, useable to force a fluid out of a sachet, this embodiment being useable in particular in the reservoir filling device shown in FIGS. 6 and 7 of the accompanying drawings, as will emerge below.

FIG. 4 shows the valve from FIGS. 2 and 3, likewise mounted on a printed circuit 7. This time, however, the charge 5 is not disposed facing a hole in the circuit and the charge 5 is therefore confined between the thinner area 8 of the substrate and the adjacent surface of the circuit 7, to which the valve is fixed by any appropriate means: welding, gluing, etc. An inflatable envelope 12, for example a flexible film of plastics material, welded to the circuit 7 at the periphery of the valve encloses the latter in the sealed space within this envelope.

As in the valve from FIGS. 2 and 3, a current flowing in the resistance 2 causes localised heating of the charge 5 by the so-called Joule effect which ignites it, generating a quantity of gas at a pressure calculated to inflate the envelope, as shown in FIG. 5. The absence of the seal 11 of the valve from FIGS. 2 and 3 will be noted, the gases generated by combustion being able to escape from the valve on all sides. The objective now is to inflate the sealed envelope 12, the benefits of which will emerge from the following description of the device shown in FIGS. 6 and 7, designed for selective automatic filling of a reservoir 10 with a liquid contained in a sachet 14 adjacent the reservoir.

In this illustrative and non-limiting example, the device from FIGS. 6 and 7 is part of an apparatus for transdermal administration of medication assisted by ionophoresis. As already mentioned in the preamble to the description, apparatus of this kind routinely includes a set of electrodes and at least one reservoir such as the reservoir 10 designed to be applied to the skin of a patient. An electrode (not shown) is joined to the reservoir 10 and cooperates with another electrode (not shown) to force ions of an active principle contained in the reservoir 10 to descend an electrical field established between the electrodes, with the result that these ions pass through the skin of the patient. The apparatus is portable and includes electronic means for controlling the field established between the electrodes and a battery power supply for these means and the electrodes. All this is familiar to the skilled person and does not require a more detailed description.

The valve of the invention can be used to produce a device of this kind in which the charging or "hydration" of the reservoir 10, for example a layer of hydrogel, with an ionic solution of active principle contained in a sachet 14 adjacent the reservoir 10 is initiated automatically by the electronic control means of the apparatus, before the treatment commences.

To this end the sachet 14 and the reservoir 10 are fixed to opposite sides of a flexible film 15 adapted to carry a circuit for energising valves in accordance with the invention. A first valve 16 is fixed to the film 15, like the valve from FIGS. 4 and 5, in a central position, for example, inside the sachet 14, and a plurality of other valves $17_1$, $17_2$, ..., $17_i$, etc, are mounted on the same film around the valve 16, like the valve from FIGS. 2 and 3. A flexible envelope 18 is welded to the film 15 and to the sachet 14 at their common periphery (see FIGS. 6 and 7), the valves $17_i$ also clamping the envelope 18 against the film 15 where they are fixed to this film.

The latter carries conductive tracks (not shown) connected to the contacts 3, 4 of the valves 16 and $17_i$, the passage of a current between these contacts being selectively commanded by the electronic means referred to hereinabove.

When these means ignite the combustible charges contained in these valves, the valves $17_i$ each open a passage or fluid communication between the sachet 14 and the reservoir 10 through the burst thinner area of a valve and a coaxial hole pierced in the film 15 while the gases generated by the combustion of the charge of the valve 16 inflate the envelope 18 (see FIG. 7). The latter then occupies a major part (or even the entirety) of the interior volume of the sachet 14, expelling the ionic solution 19 contained in the latter, this solution therefore being forced into the reservoir 10 through the valves $17_i$ and the coaxial holes pierced in the film 10, the valves $17_i$ having been opened previously by appropriate electrical commands issued by the electronic means.

Thus these means, which command the execution of a medication administration programme after the "hydration" of the reservoir, also trigger this hydration, prior to the treatment, without any human intervention such as the operation of a syringe, the tearing of a tearable envelope, etc being necessary to assure hydration. This makes this operation more reliable. The equipment employed is sealed more effectively because it is not necessary to pierce or to tear a flexible envelope to bring about hydration. The emptying of the sachet 14 can be adjusted by precise inflation of the envelope 18 which charges the hydrogel of the reservoir with a definite quantity of the ionic solution, assuring that this charging is reproducible from one set of electrodes to another.

A method of fabricating the miniature valve of the invention will now be described with reference to FIGS. 8A through 8E of the accompanying drawings. The invention advantageously employs layer forming and micro-etching technologies that are well known in the fabrication of integrated circuits, enabling these valves to be fabricated at low cost and with highly reproducible performance.

A silicon wafer (see FIG. 8A) is strongly doped on one side to confer upon it $P^{++}$ type conductivity to a depth of approximately 2 μm, for example. Both faces of the wafer are then electrically insulated with 0.5 μm layers of silicon dioxide ($SiO_2$) in turn covered with 0.5 μm layers of N-doped polycrystalline silicon (poly Si). The polycrystalline layer is on the same side of the silicon substrate as the $P^{++}$ doped layer and is then plasma etched to delimit the filamentary resistance 2 (seen in cross-section in FIG. 8B).

The resistance is then protected by oxidising the surface of the polycrystalline silicon, to form a surface layer of $SiO_2$ merging beyond the resistance 2 with the underlying layer of $SiO_2$ (see FIG. 8C). Gold contacts 3, 4 are formed at the ends of the resistance 2 by a conventional metalisation process.

After plasma etching a mask in the $SiO_2$ layers formed on the other face of the wafer and etching the crater 6 in the underlying silicon as far as the etch stop layer consisting of the $P^{++}$ layer, the silicon wafer is cut along the cutting lines 20, 20' to separate the chip shown in FIGS. 8D and 8E, respectively in plan view and in section taken along the line VIII—VIII. All that remains is to deposit a drop of nitrocellulose on top of the resistance 2 and between the contacts 3, 4, or to glue a piece of nitrocellulose film between these two contacts, to complete a miniature valve in accordance with the invention with its combustible charge.

Alternatively, the $P^{++}$ doped layer and the $SiO_2$ layer that covers it (see FIG. 8A) can be replaced with a single layer of $SiO_2$ about 3 μm thick. This then serves as the etch stop layer and as the electrical insulation layer for the resistance 2.

Problems have been, however, encountered with silica membranes. Compression stresses exceeding 0.1 GPa have been observed in such membranes. A stress this high can cause major deformation of the membrane. A deformation of 40 μm across a membrane 1 μm thick has been observed and measured, for example. Deformation on this scale can cause the membrane to rupture. This leads to a high reject rate in industrial mass production.

We refer to FIGS. 9A to 9E of the accompanying drawing to describe a variation of the manufacturing method disclosed above in connection with FIGS. 8A to 8E, this variation permitting an industrial manufacture of the miniature valve according to the invention, with a very low or even zero reject rate.

This method starts from a generally plane silicon chip the substrate 1. A respective layer $22_1$, $22_2$ of silica is formed on each of the two opposite faces of the chip (see FIG. 9A), for example by thermal oxidation of the silicon at 1 150° C. in a moist atmosphere. The thickness of the silica layer is typically between 0.5 and 1.5 μm.

As mentioned above, a compressive stress in the order of 0.27 GPa is observed in a silica layer of this kind deposited on a silicon substrate that is capable of deforming and breaking the layer where the latter is deprived of its silicon support, as in the thinner area 8 (see FIG. 2).

In accordance with the present invention, the effects of the existence of this compression stress are substantially eliminated by covering the silica layer with a layer of silicon nitride in which there is a tensile stress. By combining the effects of these contrary stresses, the residual stress in the thinner area 8 can be reduced to a level that cannot deform or rupture this area during the manufacture of the miniature valve, this level being typically less than ±0.1 GPa, the symbols + and − being attached constituting to tensile and compressive stresses, respectively. This result can be obtained by appropriately adjusting the thicknesses of the two layers using the equation:

$$\sigma_r = \frac{e_{ox} \cdot \sigma_{ox} + e_{nit} \cdot \sigma_{nit}}{e_{ox} + e_{nit}}$$

where $\sigma_r$, $\sigma_{ox}$, $\sigma_{nit}$ are respectively the residual stress in the thinner area, the compressive stress in the silica layer and the tensile stress in the silicon nitride layer, and $e_{ox}$, $e_{nit}$ are respectively the thicknesses of the silica and silicon nitride layers.

The stresses mentioned hereinabove can be measured from the deformations undergone by a 7.5×7.5 cm silicon wafer upon deposition onto the latter of one of the layers used.

In the step of the method of the invention shown in FIG. 9B layers $23_1$, $23_2$ of silicon nitride are respectively formed on the silica layers $22_1$, $22_2$.

The latter can be stoichiometric silicon nitride $Si_3N_4$. The $Si_3N_4$ layer can be formed by low-pressure vapour phase deposition at 750° C. from dichlorosilane $SiH_2Cl_2$ and ammonia. Tensile stresses in the order of 1.2 GPa able to compensate the compressive stress in the adjacent silica layer have been observed in a layer of this kind. However, the high level of this stress is responsible for mediocre adhesion of the $Si_3N_4$ layer to the silica layer, which has an unfavourable effect on the reject rate obtained in mass production.

In accordance with the present invention the reject rate is considerably improved by replacing the layer of stoicheometric nitride with a layer of silicon nitride $SiN_x$ doped with silicon, x being less than 1.33. The tensile stress (0.6 GPa) observed in a layer of this kind is lower than that observed in the stoicheometric nitride, which eliminates the adhesion problem referred to above and reduces the reject rate to a very low level, even to zero.

A silicon nitride layer enriched with silicon in this way can be formed by low-pressure vapour phase deposition at around 750° C. from silicon hydride $SiH_4$ and ammonia.

In a preferred embodiment of the present invention x=1.2 approximately. The composition of $SiN_{1.2}$ can be deduced by measuring the refractive index of the layer by ellipsometry at 830 nm.

After depositing a silica layer and a silicon nitride layer onto each face of the substrate in this way, preferably enriched with silicon, having thicknesses predetermined in accordance with the considerations discussed hereinabove, the manufacturing method of the invention continues with the formation on one face of the substrate of a filamentary resistance 24 (see FIG. 9C) by the conventional method of depositing a layer of polycrystalline silicon and then etching this layer to delimit said resistance. The latter typically has a cross-section of 0.5×100 μm and a length of 1.5 mm. Metal contacts (not shown) are formed at the ends of the resistance to enable it to be supplied with electrical energy, like the contacts 3, 4 of the valve shown in FIG. 1. The resistance 24 formed in this way is well insulated by this support, the silicon nitride layer, which is a dielectric material.

A window 25 is then formed in the layers $22_2$ and $23_2$ on the other face of the substrate, using the conventional masking and $CF_4$ gas plasma etching process. A crater 6 similar to that shown in FIG. 1 is then etched through the window 25 using an appropriate anisotropic etchant such as trimethylammonium hydroxide (see FIG. 9D). The etching is stopped by the silica layer $22_1$. The resistance 24 is then carried by a two-layer thinner area, or membrane, in accordance with the present invention (see FIG. 9E).

The miniature valve is then completed by depositing a charge of combustible material onto the resistance 24 and then mounted on a printed circuit, as in the valve shown in FIG. 2. As an illustrative and non limiting example, said charge can be made of a propergol based on glycidyl polyazide.

Two-layer membrane valves in accordance with the invention have been made with three different configurations, namely:
1) a 1 μm thick silica layer associated with a 0.22 μm layer of $Si_3N_4$;
2) a 0.5 μm thick silica layer associated with a 0.22 μm layer of $SiN_{1.2}$;
3) a 1.4 μm thick silica layer associated with a 0.6 μm layer of $SiN_{1.2}$.

Although the reject rate with configuration 1) was substantial, it had dropped to 5% and to 0% with configurations 2) and 3), respectively.

It therefore appears that associating a silica layer and a layer of $SiN_{1.2}$ achieves the essential aim of the present invention, namely production of miniature valves including a miniature resistance carried by a very thin (for example 0.7 to 2 μm thick) membrane which can be manufactured with a very low or even zero reject rate.

Moreover, measurements have shown that the thermal characteristics of the resistance mounted in this way are very good, the resistance being able to increase the temperature of the combustible charge made of the above cited propergol to 300° with an electrical power smaller than 1 W applied during less than 200 ms, which accords with another aim of the present invention.

Of course, the invention is not limited to the embodiment described and shown, which is given by way of example only. Accordingly, other semiconductor materials can be used instead of silicon for the substrate of the valve, for example germanium. Combustible materials other than nitrocellulose can be used for the combustible charge, for example other "pyrotechnic" materials. Fabrication techniques other than those used in the fabrication of integrated circuits can also be used to make the valve of the invention.

Equally, the invention extends to applications other than charging a reservoir with an ionic solution of medication for transdermal application assisted by ionophoresis. Thus the invention also finds an application in charging a reservoir used for conventional passive transdermal administration. More generally, it extends to any application in which fluid communication must be provided without mechanical access to the valve initiating this communication, for example in subcutaneous, vascular or muscular medication administration implants.

What is claimed is:

1. Miniature valve comprising a) a substrate, b) a charge of a combustible material disposed on top of the substrate facing a passage to be opened through the substrate, c) an electrical resistance in contact with the combustible charge so that supplying a predetermined electrical energy to this resistance assures the combustion of the charge and the opening of the passage by localised rupture of said substrate due to the pressure of the gases of combustion of the charges.

2. Miniature valve according to claim 1, wherein the resistance is filamentary and the charge extends over and beyond the resistance so that the heat generated by the resistance supplied with said predetermined electrical energy is initially concentrated in a portion of the charge surrounding the resistance.

3. Miniature valve according to claim 2, wherein said predetermined electrical energy is less than 10 Jousles.

4. Miniature valve according to claim 1, wherein the charge and the resistance are disposed on the same side of a thinner area of the substrate, the thickness of this area being such that the pressure of the gases due to the combustion of the charge fragments this area and opens it to the passage of fluids.

5. Miniature valve according to claim 4, wherein said substrate has two substantially parallel faces, one face having a central crater recessed into said one face and closed off at the other face by said thinner area.

6. Miniature valve according to claim 5, wherein metal contacts are formed on said other face for supplying energy to the resistance from an external source of electrical energy.

7. Miniature valve according to claim 5, wherein the substrate takes the form of a semiconductor material chip and wherein said crater and said resistance are formed on the chip by micro-etching.

8. Valve according to claim 1, wherein the combustible charge consists of a nitrocellulose or propergol type material.

9. Valve according to claim 7, wherein a weight of the combustible charge is in the order of $10^{-3}$ g.

10. Valve according to claim 4, wherein said thinner area of said substrate carrying said electrical resistance comprises at least a first layer of silica and a second layer of silicon nitride on top of the first layer.

11. Valve according to claim 10, wherein the second layer is of silicon nitride enriched with silicon $SiN_x$ with X<1.33.

12. Valve according to claim 11, wherein X=1.2.

13. Valve according to claim 10, wherein the first and second layers of $SiO_2$ and $Si_3N_4$, respectively, have thicknesses of 1 μm and 0.22 μm, respectively.

14. Valve according to claim 12, wherein the first and second layers of $SiO_2$ and $SiN_{1.2}$, respectively, have thicknesses of 0.5 μm and 0.22 μm, respectively.

15. Valve according to claim 12, wherein the first and second layers of $SiO_2$ and $SiN_{1.2}$, respectively, have thicknesses of 1.4 μm and 0.62 μm, respectively.

16. Device for filling a reservoir with a fluid contained in a sachet adjacent the reservoir, comprising at least one miniature valve according to claim 1, disposed in such manner as to obstruct fluid communication between the sachet and the reservoir and control means for commanding energisation of the electrical resistance of the valve so as to cause opening of said communication to the fluid contained in the sachet through the passage opened in the substrate of the valve by the combustion of the charge that it carries.

17. Device according to claim 16, further comprising a plurality of miniature valves disposed in the same number of fluid communications between the sachet and the reservoir, the opening of each of the latter being initiated by said control means.

18. Device according to claim 16, further comprising at least one flexible envelope inside the sachet, the envelope enclosing a miniature valve according to claim 1, said control means selectively triggering the combustion of the combustible charge carried by said valve so as to inflate said envelope with the combustion gases to assist the emptying of the sachet through the at least one miniature valve disposed in fluid communications between said sachet and said reservoir.

19. Apparatus for transdermal administration of medication in which an active principle solution is initially contained in a sachet and then, prior to the commencement of a treatment, transferred into a reservoir adapted to be placed in contact with the skin of a patient, wherein said reservoir and said sachet are parts of a device in accordance with claim 16.

* * * * *